United States Patent [19]

Gordon et al.

[11] Patent Number: 5,083,743
[45] Date of Patent: Jan. 28, 1992

[54] SLIP THREAD ADJUSTABLE IN-LINE VALVE FOR STERILE FLUIDS

[75] Inventors: Marvin Gordon, East Windsor; Sheldon P. Schmidt, Paramus, both of N.J.

[73] Assignee: Whitman Medical Corporation, Clark, N.J.

[21] Appl. No.: 691,375

[22] Filed: Apr. 25, 1991

[51] Int. Cl.⁵ .................. F16D 7/04; F16K 31/50; F16K 35/02
[52] U.S. Cl. ........................................ 251/81; 74/25; 192/56 R; 251/95; 251/114; 251/115; 251/205; 251/267; 403/118; 411/301; 464/30; 464/903; 604/249
[58] Field of Search ................. 74/25, 527, 530; 251/95, 98, 114, 115, 205, 208, 209, 248, 250.5, 267, 268, 297, 319; 403/118; 411/41, 301, 302; 464/30, 37, 903; 192/56 R; 604/246, 248, 249

[56] References Cited

U.S. PATENT DOCUMENTS

| 2,918,809 | 12/1959 | Miller | 464/903 |
| 2,971,356 | 2/1961 | Reuter et al. | 464/903 |
| 3,400,558 | 9/1968 | Haines | 464/903 |
| 3,827,670 | 8/1974 | Saarem | 251/81 |
| 4,332,369 | 6/1982 | Gordon et al. | 251/114 |
| 4,471,942 | 9/1984 | Kocanowski | 251/205 |
| 4,573,658 | 4/1986 | Gordon et al. | 251/95 |
| 4,766,641 | 8/1988 | Daglow | 464/37 |
| 4,778,149 | 10/1988 | Pesovic et al. | 251/267 |
| 4,846,011 | 7/1989 | Gaffney | 464/30 |
| 4,878,860 | 11/1989 | Williams | 464/37 |

Primary Examiner—George L. Walton
Attorney, Agent, or Firm—Fleit, Jacobson, Cohn, Price, Holman & Stern

[57] ABSTRACT

A rotatable rigid material valve operator is provided having a threaded shank threadedly engaged within a threaded blind bore formed in a valve member constructed of thermo plastic elastomer having an 80-90 "SHORE" scale durometer hardness and snugly slidingly disposed within a valve body bore against rotation relative thereto, the threaded shank being rotatable relative to the valve body against axial displacement relative thereto such that rotation of the threaded shank translates into axial shifting of the valve member within the valve body bore. The compressive resiliency and thickness of the walls of the valve member defining the blind bore are such that the threaded connection between the shank and the threaded blind bore may "slip" independent of "stripping" of the threaded connection between the threaded shank and the valve body threaded blind bore when the valve member is in a limit of axial shifting thereof and the threaded shank is inadvertently further rotated, thereby retaining the threaded connection between the threaded shank and the valve member threaded blind bore for subsequent axial adjustment of the valve member by its threaded connection with the threaded shank.

13 Claims, 1 Drawing Sheet

SLIP THREAD ADJUSTABLE IN-LINE VALVE FOR STERILE FLUIDS

BACKGROUND OF THE INVENTION

1. Field of the Invention

This invention relates to a fluid flow control valve in a system for parenteral fluid in fusion. More specifically, the instant invention relates a rigid material rotatable valve operator enjoying a threaded connection with the associated valve member and wherein the valve member is constructed of a material in the 80-90 ("SHORE" scale) durometer range and which is compressively deformable such that continued rotation of the rigid valve operator subsequent to the valve member reaching one of its two limit positions will result in "slippage" of the threaded connection between the rigid valve operator and the valve member rather than the threaded connection between the valve operator and valve member being "stripped".

2. Description of Related Art

Various different in-line valves for administering and parenteral liquids heretofore have been provided such as those disclosed in U.S. Pat. Nos. 4,332,369, 4,471,942 and 4,573,658. In each instance, however, these adjustable in-line valves include threaded connections which are susceptible to being "stripped" in the event the rotatable operator for the valve continues to have manual torque applied thereto after the associate valve member has reached one of its limit positions. Accordingly, a need exist for a threaded connection incorporated into a in-line valve for administering parenteral liquids which may not accidentally "stripped".

SUMMARY OF THE INVENTION

The adjustable in-line valve of the instant invention for administering parenteral liquids is constructed in a manner utilizing a threaded connection between a rigid, threaded valve operator and a threaded valve member wherein the valve operator includes a threaded shank threadedly engaged in a threaded blind bore formed in the valve member and further wherein the valve member is constructed of a thermo plastic elastomer having an 80-90 ("SHORE" scale) durometer hardness rating and wherein the thermo plastic elastomer is appreciably compressively deformable and the threaded connection between the threaded shank and the threaded blind bore is such that "slippage" of the threaded connection may occur independent of "stripping" of the threads comprising the threaded connection between the operator shank and the blind bore in the valve member.

By creating a threaded connection which may "slip" as opposed to "strip" threads of the threaded connection, inadvertent excess turning of the valve operator in either direction after the associated valve member has reached a limit position thereof will not render the valve inoperative for further usage.

In addition, the valve of the instant invention includes a double sealing construction thereof whereby leakage of fluids from the interior of the valve to the exterior thereof is eliminated and contamination of fluids flowing through the valve from the exterior thereof will be eliminated.

The main object of this is to provide an in-line valve for administering parenteral liquids and wherein the valve includes a threaded connection for opening and closing the same, but which threaded connection may not be "stripped" but which, upon continued rotation of the rotatable operator therefore subsequent to the associated valve member reaching a limit position thereof, may "slip" and thus retain the threaded connection for subsequent adjustment of the valve member.

Another object of this invention is to provide an in-line valve in accordance with the immediately preceding object and constructed in a manner whereby a double seal is provided between the interior of the valve and the exterior thereof in order to prevent leakage of liquids passing through the valve to the exterior thereof and contamination of the liquids passing through the valve from the exterior of the valve.

A final object of this invention to be specifically enumerated herein is to provide an in-line valve in accordance with the preceding objects and which will conform to conventional forms of manufacture, be of simple construction and easy to use so as to provide a device that will be economically feasible, long-lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENT

Figure 1:
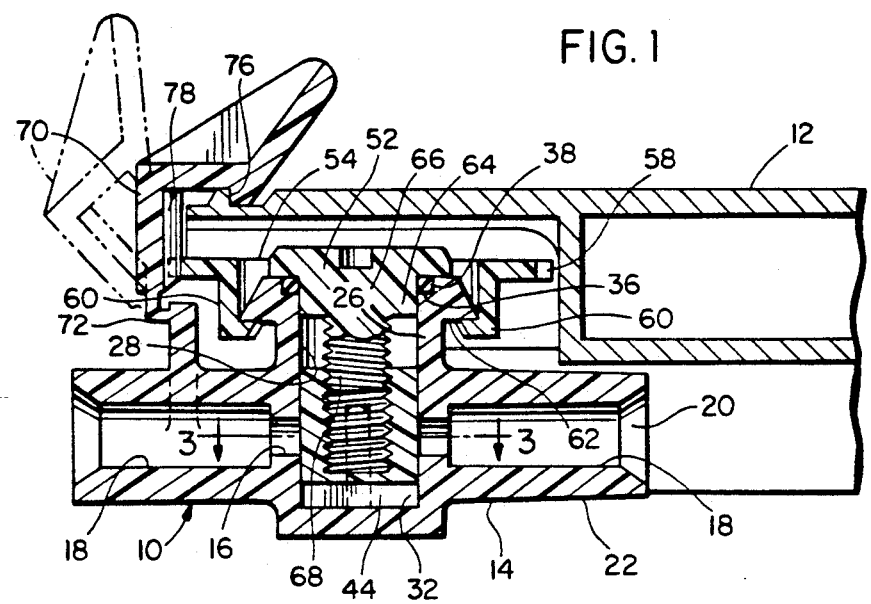
FIG. 1 is a vertical sectional view of the in-line valve of the instant invention in operative association with a handle member (fragmentarily illustrated) from which the valve is supported.
Figure 2:
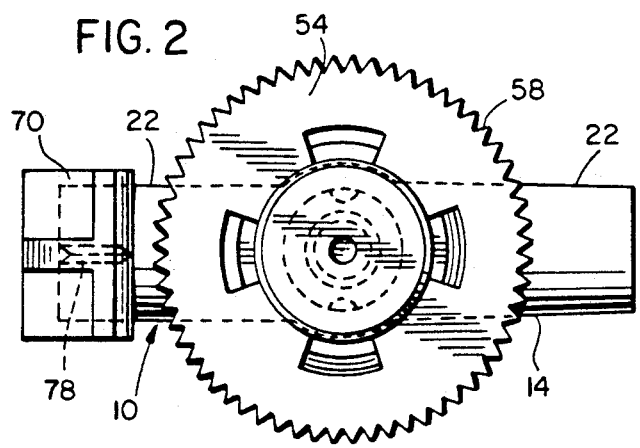
FIG. 2 is a top plan view of the valve assembly with the rotatable valve operator lock in the phantom line position of FIG. 1.

Referring now more specifically to the drawings the numeral 10 generally designates an adjustable in-line valve removably supported from a handle member 12. The specific manner of removable support of the valve 10 from the handle 12 is unimportant to the instant invention, but may similar to the manner in which the corresponding valve of U.S. Pat. No. 4,471,942 is supported its associated handle.

The valve 10 includes an elongated body 14 defining a longitudinal bore 16 extending centrally therethrough, opposite ends of the bore 16 including diametrically enlarge counterbores 18 with the remote ends of the counterbores flared as at 20. The opposite ends of the body 14 define nipples 22 over which suitable tubing sections (not shown) may be sealingly, telescopingly engaged.

As viewed in FIG. 1, the upper side of the body 14 includes an integral upwardly projecting tubular nipple 26 defining a transverse cylindrical passage or bore 28 therethrough which opens downwardly into the bore 16. The passage 28 includes a first end portion 30 disposed above the bore 16 and a second end portion 32 disposed below the bore 16. The upper end of the tubular nipple 26 terminates upwardly in an annular end face 34 co-axial with and normal to the passage 28. In addition, the upper end of the passage 28 includes a shallow counterbore 36 with the radial and axial extent of the counterbore 36 being generally equal and an O-ring 38 seated in the counterbore 36 with the axial and radial dimensions of the O-ring 38 being slightly greater than the axial and radial dimensions of the counterbore 36.

Figure 4:
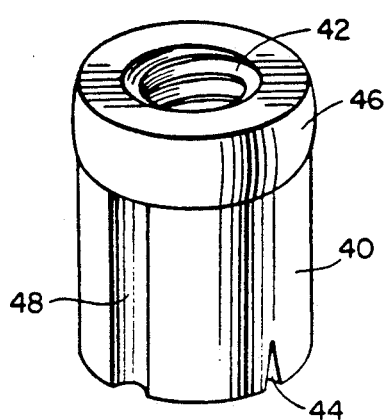
FIG. 4 is an enlarged perspective view of the valve member.
Figure 5:
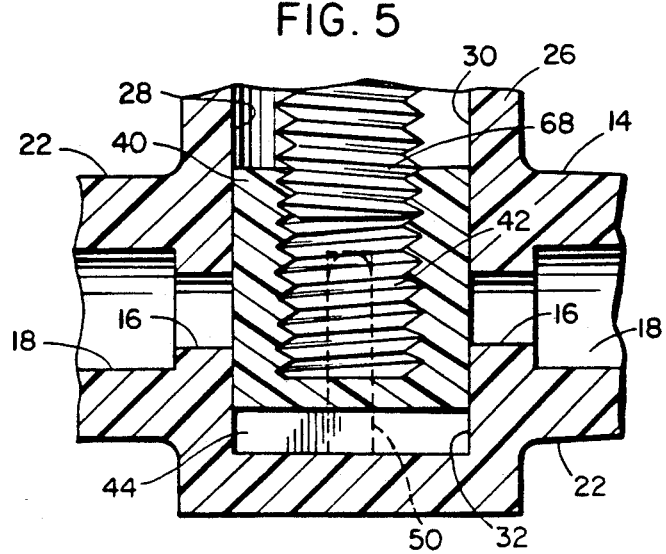
FIG. 5 is an enlarged fragmentary vertical sectional view of the central area of FIG. 1 illustrating the threaded connection between the rigid threaded shank of the rotatable operator and the threaded blind bore in the compressively deformable valve member at a point with the valve member in a fully downwardly seated position and the threaded connection between the operator shank and the valve member approaching relatively rotated positions at which the threaded connection will "slip".

A generally cylindrical valve member 40 (see FIG. 4) is provided and includes a central threaded blind bore 42 formed therein having left hand threads. In addition, the valve member 40 includes a diametric notch 44 formed therein below the lower end of the blind bore 42 and the upper end portion of the cylindrical valve body includes a circumferentially extending and axially rounded shoulder 46 of slightly greater maximum diameter than the diameter of the valve member 40 below the shoulder 46, the increased diameter of the shoulder 46 being slightly exaggerate in FIG. 4. Also, the valve member 40, below the shoulder 46, includes diametrically opposite axially extending grooves 48.

Figure 3:
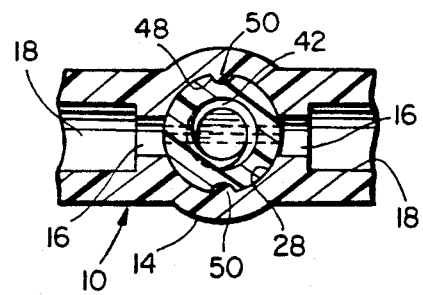
FIG. 3 is a fragmentary horizontal sectional view taken substantially upon the plane indicated by the section line 3—3 of FIG. 1.

The lower end of the transverse cylindrical passage 28 includes diametrically opposite and axially extending ribs 50 projecting inwardly of the passage 28 and the valve member 40 is snugly downwardly receivable in the transverse cylindrical passage 28 with the ribs 50 slidingly received in the grooves 48, see FIGS. 1 and 3, whereby the valve member 40 is axially shiftable in the passage 28, but non-rotatable therein.

A valve operator 52 is provided and includes a disc 54 comprising a thumb wheel and including a planar undersurface which overlies and slidingly contacts the end face 34 of the tubular nipple 26, the outer periphery of the thumb wheel or disc 54 being serrated as at 58. The disc 54 further includes peripherally spaced and inwardly turned depending integral hooks 60 which releasably hook under and slidably engage the outer periphery of a downwardly facing shoulder 62 on the exterior of the upper portion of the tubular nipple 26. The O-ring 38 is somewhat vertically compressed in the counterbore 36 by the undersurface 56 of the disc 54 and is thus radially expanded into engagement with the wall of the counterbore 36 and the adjacent smooth cylindrical outer periphery 64 of the upper end of the shank 66 of the valve operator 52 which projects down into the upper end of the transverse cylindrical passage 28. The lower end of the shank 66 is diametrically reduced and externally threaded as at 68 and threadedly engaged in the blind bore 42.

Inasmuch as the disc 54 abuts the end face 34 and the hooks 60 engage beneath the shoulder 62, the disc 54 is prevented from shifting axially of the transverse cylindrical passage 28. Therefore, rotation of the disc 54 by the serrations 58 on its outer periphery translates into axial displacement of the valve member 40 in the passage or bore 28. When the valve member 40 is in the lowest position thereof illustrated in FIG. 1 the notch 44 is disposed below the bore 60 and the latter is closed to the flow of fluid therethrough. In addition, at least one thread (preferably two) of the diametrically reduced lower end 68 of the shank 66 is threadedly engaged in the top of the blind bore 42 when the valve member 40 is in its lower limit position.

The body 14 includes a latch lever 70 hingedly supported from the body 14 as at 72 by a "living hinge" and latchable in a groove 76 formed in the handle 12. When the latching lever 70 is in the solid line position thereof illustrated in FIG. 1, a rib 78 carried by the latching lever 70 engages in one of the serrations 58 in order to lock the disc 54 against rotation relative to the body 14.

However, if before the latching lever 70 is releasably latched in the latching position thereof illustrated in solid lines in FIG. 1 the disc 54 is rotated further in a direction which would normally further downwardly displace the valve member 40, the valve member, being constructed of a compressively deformable thermo plastic elastomer having a ("SHORE" scale) 80-90 durometer hardness, is subject to radial compression and flexure such that the threaded connection between the lower end portion 68 of the rigid shank 66 (constructed of a hard polypropylene) and the valve member 40 "slip" rather than "strip" without damaging the threads on either the lower end portion 68 or within the blind bore 42.

Inasmuch as the threaded connection between the lower end 68 of the shank 66 and the valve member 40 is capable of "slipping" before the threads of the blind bore 42 are "stripped", excessive turning of the disc 54 to lower the valve member 40 will not cause the threaded connection between the shank 66 and the valve member 40 to be destroyed and subsequent reverse turning of the disc 54 will still be capable of upwardly retracting the valve member 40 from its lowermost limit position illustrated in FIG. 1 to a elevated position wherein fluid flow through the bore 16 past the valve member 40 is possible. Also, the compressive resiliency of the walls of the valve member 40 defining the bore 42 is such that the threaded connection between the shank 66 and the blind bore 42 also may "slip" when the valve member 40 is in its uppermost position in the passage 28 against the lower extremity of the larger upper end portion of the shank 66.

In addition to the O-ring 38 forming a seal between the passage 28 and the exterior of the valve body 14 to prevent leakage of fluid flowing through the bore 16 to the exterior of the body 14 or contamination of the fluid flowing through the bore 16 from the exterior of the body 14, the slightly diametrically enlarged shoulder 46 on the upper end of the valve member 40 ensures a second fluid tight seal between the valve member 40 and the walls of the transverse cylindrical passage 28. Thus, a double fluid seal is provided to prevent leakage of fluid within the body 14 thereof via the transverse cylindrical passage 28 and contamination of fluid flowing through the body 14 from the exterior thereof through the transverse passage 28.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An adjustable flow in-line intravenous supply conduit body defining a flow passage therethrough, said supply conduit including an elongated transverse passage therein opening into said flow passage and having a closed end portion disposed on one side of said flow passage and an open end portion disposed on the other side of said flow passage, a rotary torque input member rotatably mounted from said body, disposed over and closing the open end of said open end portion and rotatable relative to said body about an axis extending centrally along said transverse passage, said rotary torque input member including threaded shaft means rotatable therewith and centrally disposed in said transverse passage, and a flow controlling valve member non-rotatably and snugly slidably shiftable in and longitudinally of said transverse passage between a first limit position extending fully across said flow passage closing the latter and a second limit position at least partially opening said flow passage to fluid flow therethrough, said valve member including a threaded blind bore in which said threaded shaft means is threadedly received, said valve member being constructed of a compressible and deformable material having a "SHORE" hardness generally in the 80–90 durometer range, said threaded shaft means having an appreciably greater hardness than the hardness of said valve member, the compressibility and deformability of said valve member and the radial thickness of said valve member between the threaded blind bore thereof and the exterior thereof in relation to the greater hardness of said threaded shaft means being such that, when said valve member reaches either limit position by rotation of said threaded shank in the corresponding direction, continued rotation of said threaded shaft means in said corresponding direction will result in "slippage" of the threaded connection between said threaded shaft means and valve member as a result of deformation of the threads of said blind bore independent of "stripping" of either portion of said threaded connection.

2. The supply conduit body of claim 1 wherein said rotary torque input member includes a disc overlying and slidably engaged with the portions of said body disposed about the open end of said open end portion of said transverse passage and closing the latter from the exterior of said supply conduit body.

3. The supply conduit body of claim 2 wherein the open end of said open end portion of said transverse passage includes a shallow counterbore in which an O-ring is seated under axial compression by engagement from said disc.

4. The supply conduit body of claim 1 wherein said valve member, adjacent the open end of said counterbore, includes an exterior axially rounded circumferentially extending shoulder having a maximum diameter slightly greater than the diameter of said valve member below said shoulder and the radial compressive engagement of the portion of said valve member upon which said shoulder is formed within said transverse passages forms a fluid tight seal between the walls of said transverse passage and said shoulder.

5. The supply conduit body of claim 4 wherein said rotary torque input member includes a disc overlying and slidably engaged with the portions of said body disposed about the open end of said open end portion of said transverse passage and closing the latter from the exterior of said supply conduit body.

6. The supply conduit body of claim 5 wherein the open end of said open end portion of said transverse passage includes a shallow counterbore in which an O-ring is seated under axial compression by engagement from said disc.

7. The supply conduit body of claim 1 wherein said transverse passage includes at least one axially extending inwardly projecting rib adjacent the closed end of said transverse passage, said valve member including an external axially extending groove in which said rib is slidingly received.

8. The supply conduit body of claim 7 wherein the end of said groove corresponding to the open end of said counterbore terminates a spaced distance from the end of said valve member through which said blind bore opens.

9. The supply conduit body of claim 8 wherein said valve member, adjacent the open end of said counterbore, includes an exterior axially rounded circumferentially extending shoulder having a maximum diameter slightly greater than the diameter of said valve member below said shoulder and the radial compressive engagement of the portion of said valve member upon which said shoulder is formed within said transverse passages forms a fluid tight seal between the walls of said transverse passage and said shoulder, said shoulder being disposed between the end of said valve member through which the open end of said blind bore opens and said last mentioned end of said groove.

10. The supply conduit body of claim 1 wherein said supply conduit body includes a lateral tubular nipple defining said transverse passage and including an outer end through which said open end portion opens, said rotary torque input member including a disc overlying and slidably engaged with said outer end, said nipple inwardly of said outer end including radially outwardly projecting abutment surface means extending thereabout and facing away from said outer end, said disc including outer periphery hooks supported therefrom and hook engaged over and slidably engaging said abutment surface means.

11. A valve body including a valve member bore formed therein opening outwardly of said valve body at one end, a valve member snugly and slidably disposed in said valve member bore against rotation therein and for shifting of said valve member axially within said bore between first and second limit positions in said bore, a rotatable valve operator journaled from said body for rotation about an axis generally coaxial with said bore, against shifting axially of said bore and including a manual torque input portion disposed outwardly of said valve member bore open end, said valve member being constructed of a compressible and deformable material having a "SHORE" hardness generally in the 80–90 durometer range and having an axial threaded bore formed therein opening outwardly of the axial end of said valve member corresponding to said one end of said valve member bore, said valve operator including a rigid material threaded shank threadedly engaged in said threaded bore, the compressibility and deformability of said plug and the radial thickness of said plug between the threaded blind bore thereof and the exterior of said threaded plug in relation to the greater hardness of said threaded shank being such that, when said valve member reaches either limit position by rotation of said threaded shank in the corresponding direction, continued rotation of said threaded shank in said corresponding direction will result in "slippage" of the threaded connection between said threaded shank and said valve member as a result of deformation of the threads of said threaded bore independent of "stripping" of the threads of said threaded bore.

12. The valve body of claim 11 wherein said rotary torque input portion includes a disc overlying and slidably engaged with the portions of said valve body disposed about said valve member bore at said one end thereof and closing said valve member bore at said one end thereof.

13. The valve body of claim 12 wherein said one end of said valve member bore includes a shallow counterbore in which an O-ring is seated under axial compression by engagement from said disc.

* * * * *